United States Patent [19]
Alt

[11] Patent Number: 5,871,437
[45] Date of Patent: Feb. 16, 1999

[54] RADIOACTIVE STENT FOR TREATING BLOOD VESSELS TO PREVENT RESTENOSIS

[75] Inventor: Eckhard Alt, Ottobrun, Germany

[73] Assignee: Inflow Dynamics, Inc., Arlington, Va.

[21] Appl. No.: 762,739

[22] Filed: Dec. 10, 1996

[51] Int. Cl.$^6$ ..................................................... A61N 5/00
[52] U.S. Cl. .................................................................. 600/3
[58] Field of Search ............................. 600/1–8; 606/108, 606/191–98; 122/897–99

[56] References Cited

U.S. PATENT DOCUMENTS

| | | |
|---|---|---|
| 4,448,691 | 5/1984 | Davis . |
| 4,768,507 | 9/1988 | Fischell et al. . |
| 4,779,641 | 10/1988 | Charm et al. . |
| 5,059,166 | 10/1991 | Fischell et al. .............................. 600/3 |

OTHER PUBLICATIONS

Article published in Circulation entitled *Inhibition of Neoinntimal Proliferation With Low–Dose Irradiation From a β–Particle–Emitting Stent,* published Feb. 1, 1996, by John R. Laird, MD et al, vol. 93, No. 3, pp. 529–536.

*Primary Examiner*—John P. Lacyk
*Attorney, Agent, or Firm*—Blank Rome Comisky & McCauley LLP

[57] ABSTRACT

A non-radioactive metallic stent is coated with a biodegradable or non-biodegradable thin coating of less than about 100 microns in thickness selected to avoid provoking any foreign body reaction. The coating contains a radioactive source of beta emitting properties for irradiation of tissue when the stent is implanted in a blood vessel treated by angioplasty, to inhibit proliferation of smooth muscle cells in response to trauma to the wall of the blood vessel from the angioplasty, and thereby prevent restenosis of the vessel. The stent coating incorporating the radioactive source constitutes a first layer atop the surface of the stent, and the coating further includes a second layer incorporating an anti-coagulant substance to inhibit early thrombus formation of the stent. The second layer is adhered to and atop the first layer. The composite layer of the coating has a thickness of less than about 100 microns. The activity level of the radioactive source is approximately one microcurie.

4 Claims, No Drawings

RADIOACTIVE STENT FOR TREATING BLOOD VESSELS TO PREVENT RESTENOSIS

BACKGROUND OF THE INVENTION

The present invention relates generally to stents for use in maintaining a lumen of a blood vessel such as a coronary artery in which the stent is implanted open so that blood flow is not impeded to a substantial degree, and more particularly to stents which are coated with biodegradable or non-biodegradable substance(s) that incorporate a radioactive element to inhibit restenosis of the vessel that could otherwise occur in response to trauma to the vessel wall such as that attributable to an angioplasty procedure.

The benefits of angioplasty of arteries, particularly balloon angioplasty, and especially of the coronary arteries, has been amply demonstrated over the past decade. Angioplasty is effective to open occluded vessels that would, if left untreated, result in myocardial infarction or other cardiac disease or dysfunction. The benefits of the procedure are diminished, however, by restenosis rates approaching 50% of the patient population that undergo the procedure. Accordingly, a huge number of patients experiencing a successful primary percutaneous transluminal coronary angioplasty (PTCA) procedure are destined to require a repeat procedure. The patient faces an impact on his or her tolerance and well-being, as well as the considerable cost associated with repeat angioplasty.

Implantation of coronary stents in angioplasty patients has constituted a beacon in avoidance of the complication, risks, potential myocardial infarction or need for emergency bypass operation, and repeat angioplasty that would be present without the stenting procedure Indeed, to reduce the likelihood of reclosure of the vessel, it has become common practice for the physician to implant a stent in the patient at the site of the angioplasty or atherectomy procedure, immediately following that procedure, as a prophylactic measure. The stent is advanced on a balloon catheter to the designated site of the prior (or even contemporaneous) procedure under fluoroscopic observation. When the stent is positioned at the proper site, the balloon is inflated to expand the stent radially to a diameter at or slightly larger than the normal unobstructed inner diameter of the arterial wall, for permanent retention at the site. The stent implant procedure from the time of initial insertion to the time of retracting the balloon is relatively brief, and certainly far less invasive than coronary bypass surgery.

Despite its considerable benefits, coronary stenting alone is not a panacea, as studies have shown that about 30% of the patient population subjected to that procedure will still experience restenosis. Clearly, that percentage is still quite favorable compared to the approximate 50% recurrence rate for patients who have had a PTCA procedure without stent insertion at the angioplasty site. But improvement is needed. Also, risks of inflammation of the vessel wall and of attachment of thrombi at the site are exacerbated by the presence of the stent.

A stent is typically composed of a biologically compatible material (biomaterial) such as a biocompatible metal wire of tubular shape or metallic perforated tube. The stent should be of sufficient strength and rigidity to maintain its shape after deployment, and to resist the elastic recoil of the artery that occurs after the vessel wall has been stretched. After the stent is inserted into the vessel, its very presence in the blood stream may induce a local or even systemic activation of the patient's hemostase coagulation system. When stents are used in blood vessels of less than about 3 millimeters (mm) diameter, such as the coronary arteries, the incidence of complications increases to an even greater extent.

In the past few years, considerable research has been devoted worldwide to studying the mechanisms of restenosis. The applicant in this application has been engaged in research indicating that local thrombus formation is one of the aspects that promote restenosis. Animal research conducted by the applicant has shown that a further 30% reduction in the restenosis rate (i.e., the rate of recurrence) may be achieved if the stent is coated with a biocompatible, non-foreign body-inducing, biodegradable polylactic acid of thin paint-like thickness in a range below 100 microns, and preferably about 10 microns thick. This thin coating on a metallic stent may be used to release drugs incorporated therein, such as hirudin and/or a platelet inhibitor such as prostacyclin ($PGI_2$), a prostaglandin. Both of these drugs are effective to inhibit proliferation of smooth muscle cells, and decrease the activation of the intrinsic and extrinsic coagulation system. Therefore, the potential for a very significant reduction in restenosis has been demonstrated in these animal experiments.

In a related invention of the present applicant, described in co-pending patent application Ser. No. 08/798,333, a stent to be implanted in the body is coated with a substance or composition that undergoes continuous degradation within the body so that it acts to self-cleanse the surface as well as to release thrombus inhibitors incorporated in the coating. Degradation of the carrier occurs slowly through hydrolytic, enzymatic or other degenerative processes. Instead of the rapid formation of thrombi from contact with blood as was typically encountered with prior art techniques, the new biodegradable coating and its carrier are effective to prevent the adhesion of thrombi to the biomaterial or the coating surface. This is especially true with the addition of inhibitors that undergo slow release with the controlled degradation of the carrier. Blood components such as albumin, adhesive proteins, and thrombocytes, can adhere to the surface of the biomaterial, if at all, for only very limited time because of the continuous cleansing action along the entire surface that results from the ongoing biodegradation.

Materials used for the biodegradable coating and the slow, continuous release of drugs incorporated therein include synthetic and naturally occurring aliphatic and hydroxy polymers of lactic acid, glycolic acid, mixed polymers and blends. Alternative materials for those purposes include biodegradable synthetic polymers such as polyhydroxybutyrates, polyhydroxyvaleriates and blends, and polydioxanon, modified starch, gelatine, modified cellulose, caprolactaine polymers, acrylic acid and methacrylic acid and their derivatives. It is important that the coating have tight adhesion to the surface of the biomaterial, which can be accomplished by applying the aforementioned thin, paint-like coating of the biodegradable material that may have coagulation inhibitors blended therein, as by dipping or spraying, followed by drying, before implanting the coated biomaterial device.

Two or more different drugs suitable for inhibiting coagulation may be incorporated into the carrier to provide a synergistic effect with release as the coating slowly disintegrates, as where one substance inhibits plasmatic coagulation and another inhibits platelet-induced, cellular coagulation. Hyperplasia is inhibited or suppressed as well, and infection is not prevalent even when the coating is applied to the biomaterial under non-aseptic conditions.

Hirudin is a naturally occurring and potent thrombin inhibitor that may be incorporated into the carrier with very beneficial results. Similar results are achievable with natural or synthetic prostaglandin derivative instead of or in addition to the hirudin. Specific platelet inhibitors that act on the GP IIb/IIIa receptor are especially helpful in preventing platelet activation following coronary interventions. Anti-adhesive peptides are also suitable, especially with thrombocyte aggregation inhibitors. Inhibition of adhesive proteins which function as bridging proteins tends to preclude adhesion and aggregation of thrombocytes. Locally effective, naturally occurring fibrinolytic substance such as Urokinase, r-TPA or Streptokinase, when added to the coating carrier for slow release, enhance continuous self-cleaning of the surface.

Anti-proliferation substances may be incorporated into the coating carrier to slow proliferation of smooth muscle cells at the internal surface of the vascular wall. Such substances include corticoids and dexamethasone, which prevent local inflammation and further inducement of clotting by mediators of inflammation. Substances such as tamoxifen and other cytostatic drugs directly interfere with intimal and medial hyperplasia, to slow or prevent restenosis, especially when incorporated into the coating carrier for slow release during biodegradation. Local relaxation of a vessel can be achieved by inclusion of nitrogen monoxide (NO) or other drugs that release NO, such as organic nitrates or molsidomin.

A slow release of drugs is used to prevent thrombus formation according to another of applicant's inventions in this field, and also to inhibit inflammatory responses and restenosis of the blood vessel, such as a coronary artery in which a stent is implanted following angioplasty. One factor that contributes to restenosis is the production of new arterio- or artherosclerotic material within the intimal and medial layers, analogous to would healing and scar tissue. Another contributing factor is the mechanical or elastic recoil of the artery, particularly the outer layer of the vessel wall, with resulting loss of lumen diameter. Stenting of the artery alone provides improved results over a pure PTCA procedure (where the intimal arteriosclerotic masses are squeezed and the outer layer is slightly enlarged) by stabilizing the artery and preventing recoil by virtue of the rigid structure of the metal stent.

According to that invention, the amount and dosage of the drug(s) incorporated into and released from the biodegradable carrier material is adjusted to suppress the thrombotic and restenotic processes only locally while allowing effective clotting of the blood systemically. In performing those functions, the method provides a biodegradable carrier into which is incorporated one or a combination of drugs for synergistic suppression of thrombus formation and restenosis development from plasmatic coagulation as well as at the cellular level in a dosage giving a sufficient local action but avoiding systemic action on the coagulation system.

The active period of the coated stent may be adjusted by varying the thickness of the coating, the specific type of biodegradable material selected for the carrier, and the specific time release of incorporated drugs or other substances selected to prevent thrombus formation or attachment, subsequent restenosis and inflammation of the vessel. After an initial effective period of the coating following implantation of the stent, which should be at least in the range of from two to four weeks, and preferably three months, during which the biodegradable coating undergoes virtually complete disintegration, the undesirable effects sought to be prevented are unlikely to recur because by that time the mechanisms that led to them will have subsided or a natural cell or tissue layer of limited extent will have begun to form on the stent. The acute response is deemed to be most important, so long-term action is not particularly required. The beneficial action of this coating has been shown by the applicants herein in a recently completed animal study. Fully four weeks after its implantation in the coronary arteries of sheep, the coated stent artery was fully open and not obstructed, whereas an uncoated stent implanted at approximately the same time caused a vascular response that had already considerably reduced the lumen diameter.

The biodegradable coating may also be applied to the stent in multiple layers, either to achieve a desired thickness of the overall coating or a portion thereof for prolonged action, or to employ a different beneficial substance or substances in each layer to provide a desired response during a particular period following implantation of the coated stent. For example, at the moment the stent is introduced into the vessel, thrombus formation will commence, so that a need exists for a top layer if not the entire layer of the coating to be most effective against this early thrombus formation, with a relatively rapid release of the incorporated, potent anticoagulation drug to complement the self-cleansing action of the disintegrating carrier. For the longer term of two weeks to three months after implantation, greater concern resides in the possibility of intimal hyperplasia that can again narrow or fully obstruct the lumen of the vessel. Hence, the same substance as was present or a different substance from that in the top layer might be selected for use in the application of the coating to meet such exigencies. Hirudin is an example of a substance that can be effective against both of these mechanisms or phenomena.

The experiments performed by the applicant have shown that the degree of restenosis and neointimal proliferation present at the site of stent implantation depends on the degree of vessel injury and on local vascular strain. To reduce this phenomenon, specific means are considered to inhibit smooth muscle cell growth which is the underlying cause of this restenotic process.

Aside from the prevention of local thrombus formation and incorporation of cytostatic drugs into a biodegradable carrier, as previously disclosed by applicant in a co-pending application, others have suggested the use of radiation to inhibit restenosis. Fischell et al. proposes in U.S. Pat. No. 4,768,507 the use of a special percutaneous insertion catheter for purposes of enhancing luminal dilation, preventing arterial restenosis, and preventing vessel blockage resulting from intimal dissection following balloon and other methods of angioplasty.

In U.S. Pat. No. 4,779,641 and co-pending European patent application No. 92309580.6, the use of an interbiliary duct stent is disclosed. There, radioactive coils of a wire which are embedded into the interior wall of the bile duct ostensibly to prevent restenotic processes from occurring.

U.S. Pat. No. 4,448,691 and co-pending European patent application No. 90313433.6 disclose a helical wire stent, provided for insertion into an artery following balloon angioplasty or atherectomy, which incorporates or is plated with a radioisotope. According to that patent, a radioactive stent will decrease the proliferation of smooth muscle cells. The disclosure teaches that the stent may be made radioactive by irradiation or by incorporating a radioisotope into the material of which the stent is composed. Another solution would be to locate the radioisotope at the core of the tubular stent or to plate the radioisotope onto the surface of the stent. The patent also teaches, aside from the provision of radioactivity of the stent, that an outer coating of anti-thrombogenic material might be applied to the stent.

Clinical basic science reports such as "Inhibition of neointimal proliferation with low dose irradiation from a beta particle emitting stent" by John Laird et al published in *Circulation* (93: 529–536, 1996) describe creating a beta particle-emitting stent by bombarding the outside of a titanium wire with phosphorus. The implantation of phosphorus into the titanium wire was achieved by placing the $P^{31}$ into a special vacuum apparatus, and then vaporizing, ionizing and, accelerating the ions with a higher voltage so that the $P^{31}$ atoms become buried beneath the surface of the titanium wire in a thickness of about ⅓ micron. After exposing the wire altogether with the phosphorus radioisotope for several hours to a flux of slow neutrons part of the $P^{31}$ atoms were converted into a $P^{32}$, a pure beta particle emitter with a maximum energy of 1.709 megaelectron-volts, an average of 0.695 megaelectron-volts, and a half-life of 14.6 days.

Despite the convincing clinical results obtained by this method, practical application of the method in human patients raises considerable concerns. First, it is difficult to create a pure beta emitter from phosphorus if a stent is exposed to a flux of slow neutrons. In addition to converting phosphorus from $P^{31}$ to $P^{32}$, the metallic structure of the titanium wire will become radioactive. Therefore, about 20 days are needed to allow the radiation to decay, especially gamma radiation which originates from the titanium wire. Even worse is the situation where a metal such as stainless steel undergoes radioactive irradiation, resulting in production of unwanted radiation and a wide range of short and long term radionuclei such as $cobalt^{57}$, $iron^{55}$, $zinc^{65}$, $molybdenum^{99}$, $cobalt^{53}$. A pure beta radiation emitter with a penetration depth of about 3 millimeters is clearly superior for a radioactive stent for purposes of local action, side effects and handling.

Reports have indicated that good results have been obtained with a radioactive wire inserted into the coronary arteries or into arteriosclerotic vessels of animals. Results obtained with a gamma radiation source from a wire stems from the deeper penetration of gamma radiation, which is about 10 mm. Assuming that the vessel is 3 to 4 mm in diameter, a distance of 2 to 4 mm depending on the actual placement of the wire toward a side wall has to be overcome before the radiation acts. Therefore, the clinical results that have been obtained with radioactive guide wires that have been inserted into the coronary arteries for a period ranging from about 4 to 20 minutes for delivery of a total dosage of about 8 to 18 Gray (Gy) have shown that gamma radiation has a beneficial effect while beta radiation from a wire is less favorable. On the other hand, gamma radiation which originates from a stainless steel stent such as composed of 316L is less favorable since the properties of β radiation such as a short half life and a short penetration depth is superior to γ radiation originating from radioactive 316L with a long half-life and a deeper penetration since the proliferative processes of smooth muscle cell proliferation occur within the first 20 to 30 days and only in the very close vicinity of the stent.

In addition, a half-life which is too short such as one to two days considerably impacts on logistics if a metallic stent needs to be made radioactive. That is, by the time the stent is ready for use, its radioactivity level may have decayed to a point which makes it unsuitable for the intended purpose.

A discussion of the irradiation of nickel-titanium or steel is found in German patent P 4315002 issued to Christoff, and corresponding PCT application EP 94-01373 which corresponds to EP 94 916177.2, reporting on a metallic stent with a short and a long half-life.

While the prior art reports on various ways to made a metallic stent radioactive, for the purpose of practical use it is assumed that the availability of a non-radioactive metallic stent has considerable advantages. It is a principal aim of the present invention to provide a method to provide radioactivity without incorporating the radioactive material into a metallic stent or irradiating the stent itself. In this way, the radioactivity can be more easily integrated, manufactured, maintained, controlled, distributed, and so forth, than is possible with a radioactive metallic stent that is produced by the usual known methods.

SUMMARY OF THE INVENTION

According to the invention, a metallic stent is coated with a biodegradable or non-biodegradable coating which incorporates a beta emitting radioactive source such as phosphorus $P^{32}$ with a radioactivity level of about one microcurie. Preferably, phosphorus in organic form is obtained for low level radiation test purposes in a microcurie range, and can be easily blended into a chloroform or solvent of a polylactic carrier. In addition, not only is the restenosis triggered by the proliferation of smooth muscle cells inhibited, but the restenosis triggered by thrombus formation can also be inhibited, by incorporating into the coating carrier not only a radioactive material such as phosphorus isotope, but also hirudin or iloprost or other anti-coagulant.

To prevent the phosphorus radioactivity from being distributed throughout the body, it is preferred that an inner coating containing the radioactive phosphorus be applied directly onto the surface of the stent, and then an outer coating applied atop the inner coating, containing substances such as an anti-coagulant or a proliferation inhibitor such as taxal or other hemotherapeutics. Thus, the coating may be applied in multiple layers to accomplish this task, each of which is allowed to dry before the next is applied.

Another aspect of the current invention is to use phosphorus in a chemical binding to a substance that is readily excreted by renal or feces function to prevent the incorporation of radioactive phosphorus into the bones and other cells where radiation is unwanted.

An important aspect of the invention that a combination of a cytostatic substance such as taxal and radiation is beneficial because the presence of the cytostatic substance causes the cell proliferation to be more organized in a certain phase that makes it more susceptible to radiation. For example, exposure to radioactivity in the presence of the cytostatic substance provides the same effect at 20% of the delivered dosage as would 100% radioactivity (i.e., with no cytostatic or comparable substance present).

DETAILED DESCRIPTION OF THE PREFERRED EMBODIMENTS AND METHODS

Preferably, the coating to be applied to a stent according to the present invention employs a biodegradable carrier which is selected to undergo a slow disintegration without harmful effect in the cardiovascular system. Such a coating carrier serves to continuously cleanse the exposed surface of the stent by removal of a microscopically thin layer of the carrier material while releasing selected drugs incorporated therein. The carrier may be selected from natural or synthetic aliphatic or hydroxy polymers of lactic acid, glycolic acid, or mixed polymers or blends thereof, or from synthetic polymers such as polyhydroxybutyrates, polyhydroxyvaleriates or blends thereof, or from polydioxanon, modified starch, gelatine, modified cellulose, caprolactaine polymers, acrylic acid or methacrylic acid or their derivatives. Alternatively, a non-biodegradable carrier may be used. A peripheral primary requirement for either such carrier is that it be sufficiently elastic and flexible to remain unruptured on the exposed surfaces of the stent despite a considerable expansion of the stent during deployment to increase the lumen diameter from, typically, 1 mm to 5 mm.

A substance which may comprise a single drug or agent, such as hirudin or a platelet inhibitor such as prostacyclin ($PGI_2$), or a proliferation inhibitor such as tacsule or other hemotherapeutics. Each of these is effective to inhibit proliferation of smooth muscle cells, and decrease the activation of the intrinsic and extrinsic coagulation system. Alternatively, a synergistic combination of agents of sufficient potency to prevent the thrombus formation, inflammation and restenosis of the vessel, can be blended into the carrier prior to application to the stent. In the preferred method, the coating containing these types of drugs is applied as the outer layer, atop an inner layer to be applied directly to the stent surface and incorporating the radioactive material such as $P^{32}$ with a radioactivity level of about one microcurie. The additive drugs or substances for the outer layer of the coating should be capable of being dissolved or dispersed in a quickly evaporating solution, such as chloroform or methyl chloride, to effect fast drying with a low boiling point.

The carrier should adhere tightly to the surface of the metal (or non-metallic) stent, and preferable this is accomplished by applying the carrier material in successive thin layers. Each layer may incorporate coagulation inhibitors, by dipping or spraying the stent in a liquid solution of the carrier of moderate viscosity. After each layer is applied, the stent is dried before application of the next layer. Particular attention should be given to drying of the final layers which incorporate the radioactive material and which together form the inner radioactive layer. It is desirable that the thin, paint-like composite coating should not exceed an overall thickness of 100 microns, and preferably is about 10 microns thick—5 microns for each of the inner layer (radioactive, to inhibit smooth muscle cell proliferation) and outer layer (anti-coagulant, to inhibit thrombus formation).

A suitable biodegradable coating solution is prepared by dissolving 480 milligrams (mg) of a drug carrier, such as poly-D, L-lactid (available as R203 of Boehringer Inc., Ingelheim, Germany) in 3 milliliters (ml) of chloroform under aseptic conditions. In principle, however, any biodegradable (or non-biodegradable) coating material that is blood and tissue compatible and can be dissolved, dispersed or emulgated, may be used as the carrier agent if, after application, it undergoes relatively rapid drying to a self-adhesive lacquer- or paint-like coating, and subsequent disintegration in a controlled manner when in contact with the blood or tissue fluids. The molecular weight of 27000 dalton of R203 has been found to best suit the requirements of both mechanical stability and elasticity to guarantee a complete coverage of the stent also in an expanded state.

Sterile active substances may be selectively incorporated in the carrier by addition to the biodegradable carrier solution for antithrombotic, anti-inflammatory, anticoagulant, anti-proliferative and/or antibiotic action. A suitable biodegradable coating material impregnated with hirudin—especially the pharmaceutical preparation of PEG hirudin (polyethylene glycol bound hirudin)—is prepared by dispersing 24 mg of finely separated hirudin power into the carrier solution under aseptic conditions, and then storing the mixture at –10° C. for subsequent application. A liquid hirudin anticoagulant drug solution may be prepared rather than powder.

Other examples of preparation of suitable biodegradable coating compositions incorporating active substances are the following. 48 mg of Iloprost (trade name for synthetic prostaglandin derivative) is dispersed under aseptic conditions into the carrier solution, and the composition is stored at –10° C. until ready to use. Prostacyclin $PGI_2$ may be used to substantially the same effect. A dexamethasone coating is prepared by introducing 4.8 mg of finely dispersed dexamethasone powder into the carrier solution. Alternatively, a liquid form of dexamethasone (available under the trade name Fortecortin in Germany), which is crystalline in solution, may be used. For an antibiotic coating, 4.8 mg of gentamicin powder is dispersed into the carrier solution. Heparin can be incorporated as an anticoagulant substance into the coating by dissolving 24 mg of heparin powder into the carrier solution, but is clearly a less favorable antithrombotic agent compared to hirudin for local application.

At times, it may be desired to have a more rapid antithrombotic action, as in cases where a critical infarction patient has a high risk of local thrombus formation by adhesion of preexisting thrombin material to the stent and resultant closure of the coronary artery when the stent is implanted. In such instances, the stent may be coated with a compound including the carrier solution with 50,000 units of urokinase powder incorporated therein, by dipping the stent into the compound solution and then drying the resultant coating on the surface of the stent. Even as such a coated stent is being introduced in the coronary artery, a fast release of the antithrombotic drug is taking place, with controlled biodegradation of the coating, to effect continuous local thrombolysis.

For the inner layer, a suitable amount of the radioactive phosphorus isotope coupled to a nonresorbable and readily excretable substance such as inulin is added to the coating carrier to provide a radioactivity level of about one microcurie or somewhat higher level for the overall inner layer of one stent of 7 mm length which is sufficient to produce the desired inhibition of hyperplasia. Because the coating process is performed in the presence of a radioactive material, albeit very low level, the portion of the process involving application of the inner layer to the stent (which, as noted above, may be applied in several thin layers to produce the thicker, preferably 5 micron inner layer) are performed with a robotic apparatus. Storage of the radioactive stent coating to the primarily nonradioactive stent is easy. Since in a distance of 10 mm to the stent, the outside of the cardboard container, less than 1% of the total radiation can only be detected making storing and handing easier.

Another aspect of the present invention is the finding that low dose cytostatic drugs released from a biodegradable carrier can inhibit smooth muscle cell proliferation and therefore prevent restenosis. Aside from this effect which has been shown in a dosage dependent effect by the applicant, cytostatic drugs can also synchronize the proliferation cycle of smooth muscle cells making these more suitable to the growth inhibitory effects of radiation. In practice, this means that low dosages of radiation and of cytostatic drugs together can exhibit the same beneficial effect on reduction restenosis as a many-fold single dose of each—radiation and cytostatic drug alone. But the combination exhibits a very low side effect profile while the beneficial effect is synergistic.

As a result of its capability to be expanded in diameter and then to remain relatively rigid, the stent is adapted to prevent elastic recoil of the vessel wall. The carrier portion of the coating is a material having a molecular chain length which renders it sufficiently elastic on the stent to preclude cracking or other disruption of the coating when the stent is deployed in the vessel. For example, the stent may have a diameter of 0.03 to 0.04 inch when it is in the unexpanded state and crimped onto the balloon catheter, and may be expanded to 2.5 to 5 millimeters when deployed, so that it may be stretched by a factor of 3 to 6. The coating must be sufficiently elastic to preclude it from cracking or becoming brittle during such deployment, that any portion of the stent biomaterial is uncoated and exposed. The R203 material referred to above has a molecular chain length which is quite adequate for these purposes.

In the coating process, the stent is preferably dipped into the sticky carrier solution (which may be moderately to highly viscous, depending on desired thickness of the coating, or applied in several coats using a spray-on thinner solution) incorporating the selected drug(s), under sterile conditions and at room temperature. Typically, only about 1 to 2 minutes are required for drying. After evaporation of the solvent (e.g., chloroform), the coating tightly adheres to the stent surface. If desired, the coating may be applied to the stent in one or more layers just before the stent is to be implanted. Rather than a premixed solution, then, the carrier may be supplied separately with mixing instructions and drugs or substances for tailoring the ultimate coating with formulas that are individually adjustable and blended by the attending physician.

Although certain preferred compositions and methods have been disclosed herein, it will be appreciated by those skilled in the art to which the invention pertains, from a consideration of the foregoing description, that variations and modifications may be made without departing from the spirit and scope of the invention. Accordingly, it is intended that the invention shall be limited only by the appended claims and the rules and principles of applicable law.

What is claimed is:

1. A method of providing a stent with the capability of localized action in placement at a treatment site of an earlier procedure for opening the lumen of a blood vessel of a patient, wherein said action is to prevent both thrombus formation on the stent and restenosis of the blood vessel in the locality of the treatment site, without substantial adverse systemic effect of the patient, said method comprising the steps of applying to an exposed surface of the stent a coating including a cytostatic drug and a radioactive substance in a carrier, in which the concentration of each of said cytostatic drug and said radioactive substance in the coating is such as to create a synergistic action between a chemical inhibition and a radioactive inhibition of restenosis so as to reduce the dosage of radiation required if acting alone, to effect the same amount of inhibition of restenosis.

2. The method of claim 1, wherein said radioactive substance is coupled to a substance which is readily excreted by the body and not stored in the body, whereby to prevent prolonged radiation at other than desired sites in the body.

3. A vascular stent, comprising a non-radioactive metallic tube having open ends and a sidewall containing a multiplicity of openings therethrough to allow said stent to be expanded radially for deployment in a blood vessel subjected to angioplasty so as to maintain the lumen of the blood vessel open for blood flow therethrough following the angioplasty procedure; and a thin coating on an exposed surface of the tube, said coating including a carrier composed of a biocompatible material and having dispersed therein a first substance characterized by radioactivity for irradiation of tissue in the blood vessel wall and a second substance constituting a cytostatic drug, said first and second substances being selected to act synergistically to inhibit restenosis of the blood vessel following the opening of the lumen thereof by the angioplasty procedure.

4. A method of preventing restenosis of a blood vessel which has undergone angioplasty to open a stenosed region of the lumen of the vessel, the method comprising inserting a stent into the blood vessel and deploying the stent to contact the vessel wall at the site of the stenosed region, and irradiating the tissue in the wall at said site with a radioactive substance in a biodegradable carrier which is not metabolized or absorbed by the body adhered to a surface of the stent so that said radioactive substance substantially dissipates in a time interval determined by the thickness of the biodegradable carrier on the stent.

* * * * *